(12) United States Patent
Plakogiannis et al.

(10) Patent No.: US 9,138,402 B2
(45) Date of Patent: *Sep. 22, 2015

(54) ARIPIPRAZOLE COMPOSITIONS AND METHODS FOR ITS TRANSDERMAL DELIVERY

(75) Inventors: Fotios M. Plakogiannis, Whitestone, NY (US); Muhammed Anwar Hossain, Congers, NY (US)

(73) Assignee: Transdermal Research Pharm Laboratories, LLC, Whitestone, NY (US)

( * ) Notice: Subject to any disclaimer, the term of this patent is extended or adjusted under 35 U.S.C. 154(b) by 91 days.

This patent is subject to a terminal disclaimer.

(21) Appl. No.: 13/879,485

(22) PCT Filed: Oct. 20, 2011

(86) PCT No.: PCT/US2011/057080
§ 371 (c)(1),
(2), (4) Date: Apr. 15, 2013

(87) PCT Pub. No.: WO2012/058091
PCT Pub. Date: May 3, 2012

(65) Prior Publication Data
US 2013/0209552 A1    Aug. 15, 2013

Related U.S. Application Data

(60) Provisional application No. 61/407,591, filed on Oct. 28, 2010.

(51) Int. Cl.
*A61F 13/00* (2006.01)
*A61K 9/00* (2006.01)
*A61K 9/06* (2006.01)
*A61K 9/08* (2006.01)
*A61K 31/496* (2006.01)
*A61K 47/10* (2006.01)
*A61K 47/32* (2006.01)
*A61K 47/44* (2006.01)

(52) U.S. Cl.
CPC ............... *A61K 9/0014* (2013.01); *A61K 9/06* (2013.01); *A61K 9/08* (2013.01); *A61K 31/496* (2013.01); *A61K 47/10* (2013.01); *A61K 47/32* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 7,807,680 B2 * | 10/2010 | Kostanski et al. | 514/253.07 |
| 2004/0170672 A1 * | 9/2004 | Selzer | 424/449 |
| 2007/0032651 A1 | 2/2007 | Salama et al. | |
| 2008/0112986 A1 | 5/2008 | Kostanski et al. | |
| 2009/0156813 A1 | 6/2009 | Aronhime et al. | |
| 2010/0015195 A1 * | 1/2010 | Jain et al. | 424/422 |

FOREIGN PATENT DOCUMENTS

| | | | |
|---|---|---|---|
| EP | 0564307 A1 | | 6/1993 |
| WO | WO 2009/060473 | * | 5/2009 |

OTHER PUBLICATIONS

International Search Report for PCT/US2011/057080.

* cited by examiner

*Primary Examiner* — Snigdha Maewall
(74) *Attorney, Agent, or Firm* — Caesar Rivise, PC

(57) ABSTRACT

The present invention discloses compositions of liquid and gel formulation containing aripiprazole in the form of a patch for transdermal delivery.

4 Claims, 3 Drawing Sheets

ARIPIPRAZOLE COMPOSITIONS AND METHODS FOR ITS TRANSDERMAL DELIVERY

FIELD OF THE INVENTION

The present invention relates to the field of transdermal delivery of pharmaceutical compositions, which have an acceptable in vitro performance and good bioavailability. In particular, the transdermal pharmaceutical compositions of the present invention include liquids or gels of aripiprazole in a patch dosage form.

BACKGROUND OF INVENTION

Aripiprazole (ARPZ) is the first of a new class of atypical antipsychotics (third generation). Biochemically, ARPZ is a partial agonist of the D2 family of dopamine receptors.[1,2] It is active against positive and negative symptoms of schizophrenia.[3,4]

ARPZ is a quinolinone derivative, white crystalline powder, practically insoluble in water, with a low melting point (135-140° C.), MW 448,38 g/mole and partition coefficient of 4.54.

BRIEF DESCRIPTION OF SEVERAL VIEWS OF THE DRAWINGS

The invention will be described in conjunction with the following drawings wherein.

DESCRIPTION OF THE INVENTION

Example

ARPZ is practically insoluble in water and has been formulated as a liquid and gel dosage form (Table 1). All reported values are in weight/volume percentage (W/V)

TABLE 1

Composition of liquid and gel formulation of Aripiprazole (5% W/V)

|  | W/V | W/V |
| --- | --- | --- |
| N-methyl-2-pryolidone (NMP) | 40% | 40% |
| Dimethyl Sulfoxide (DMSO) | 40% | 40% |
| Ethyl Alcohol | 15% | 15% |
| Carbopol 971P | — | 0.5% |
| Water | 5% | 4.5% |
| Total | 100.00% | 100.00% |

An optimal mixture design of experiments was used to select the levels of the formulation variables. The optimum composition of a 1% W/V to 20% W/V ARPZ liquid formulation was predicted to have NMP 40%, DMSO 40%, Alcohol 15% and water 5% (Table 1). The gel formulation should contain a gelling agent in the range of about 0.1% to 5% W/V and the optimum APRZ composition should range from about 1% W/V to 20% W/V with about 0.5% W/V of the gelling agent. Therefore, the gel formulation was predicted to have a NMP of 40%, DMSO 40%, Alcohol 15%, Carbopol 971 0.5%, and Water 4.5% (Table 1). However, Table 2 lists other combinations that also could produce successful liquid and gel ARPZ formulations in accordance with the present invention.

TABLE 2

Concentration Ranges of N-Methyl-2-Pyrolidone (NMP), Dimethl Sulfoxide (DMSO), Ethyl Alcohol, and Water in Liquid Aripiprazole Formulation

| Formulation | NMP | DMSO | Alcohol | Water |
| --- | --- | --- | --- | --- |
| 1. | 50 | 50 | — | — |
| 2. | 40 | 40 | 20 | — |
| 3. | 40 | 40 | — | 20 |
| 4. | 40 | 40 | 15 | 5 |
| 5. | 40 | 40 | 10 | 10 |
| 6. | 40 | 40 | 5 | 15 |
| 7. | 30 | 30 | 20 | 20 |
| 8. | 30 | 30 | 30 | 10 |
| 9. | 30 | 40 | 25 | 5 |
| 10. | 40 | 30 | 25 | 5 |
| 11. | 45 | 45 | 10 | 0 |
| 12. | 45 | 40 | 10 | 5 |

Other than these components, other solvents known to those skilled in the art suitable for use in the present invention can be used to prepare the liquid formulation, and combinations thereof, including but not limited to alcohols such as but not limited to (methyl, ethyl, butyl, propyl, isopropyl, isopropyl myristate, etc.), glycols such as, but not limited to (propylene, polyethylene, glycerin, etc.) mineral oils, vegetable oils, and others.

Example

Figure 1:
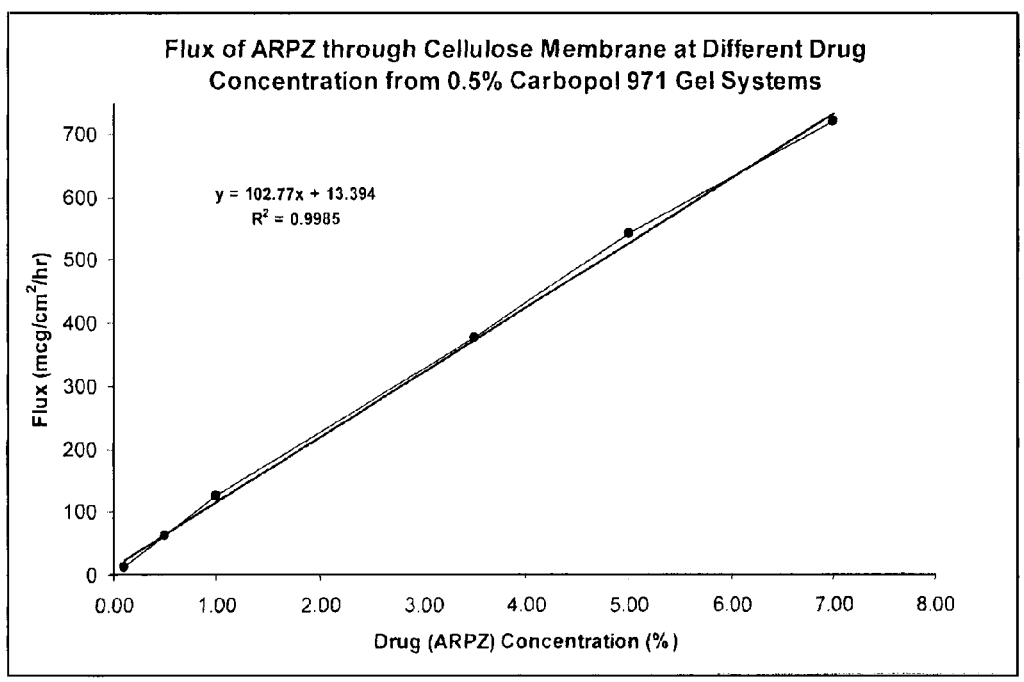
FIG. 1 is a chart showing the Effect of Drug Concentration on the Flux of ARPZ through Cellulose Membrane from 0.5% Carbopol 971 Gel Systems.
Figure 2:
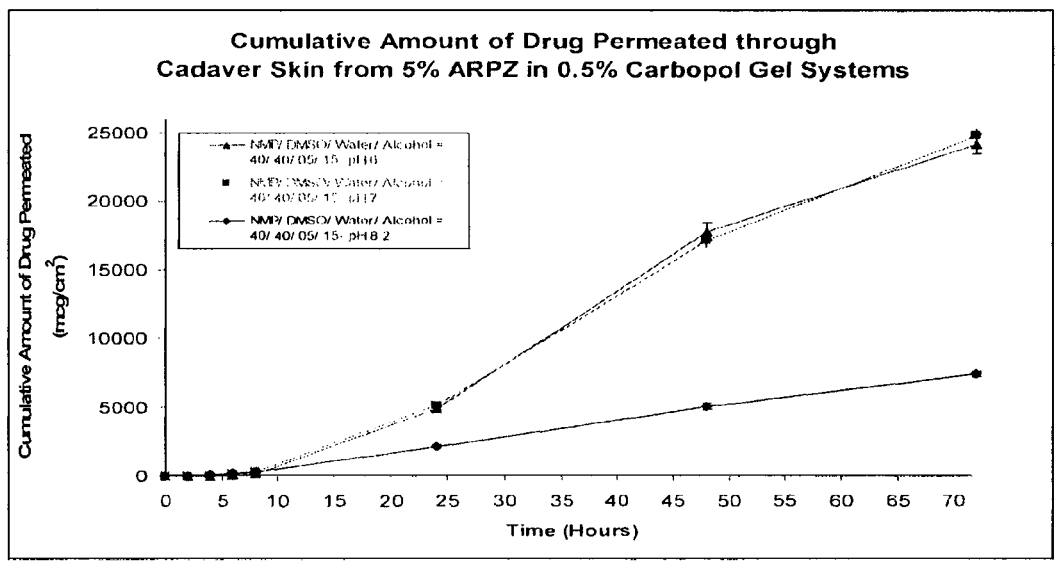
FIG. 2 is a chart showing the Cumulative Amount of 5% ARPZ Permeated through Cadaver Skin from 0.5% Carbopol Gel System.

The effect of gelling agents and their concentration on the permeation of ARPZ through artificial membranes and human cadaver skin was evaluated and two characteristic graphs are shown in FIGS. 1 & 2. The optimal desired composition of ARPZ gel formulation contains 0.5% W/V Carbopol 971. ARPZ can be gelled by gelling agents, including but not limited to, natural polymers (such as agar, alginic acid and derivatives, *cassia* tora, collagen, gelatin, gellum gum, guar gum, pectin, potassium, or sodium carageenan, tragacanth, xanthan, etc), semisynthetic polymers (such as methylcellulose, carbosymethylcellulose, hydroxypropylcellulose, hydroxypropylmethylcellulose, etc.) synthetic polymers (such as carboxyvinyl polymers or carbomers: carbopol 940, carbopol 934, carbopol 971, poloxamer, polyacrylamide, polyvinyl alcohol, polyethylene, and its co-polymers etc), and clays (such as silicates, etc). In addition, other than cellulose membranes, ARPZ can be evaluated with other artificial membranes including but not limited to silicone membranes (polydimethylsiloxane), liposome-coated membranes, solid-supported liquid membranes, lecithin organogel membranes and other. Besides the gel formulations of ARPZ, other dosage forms including, but not limited to, ointments, creams, emulsions, liposomes, etc. may be used.

Example

Figure 3:
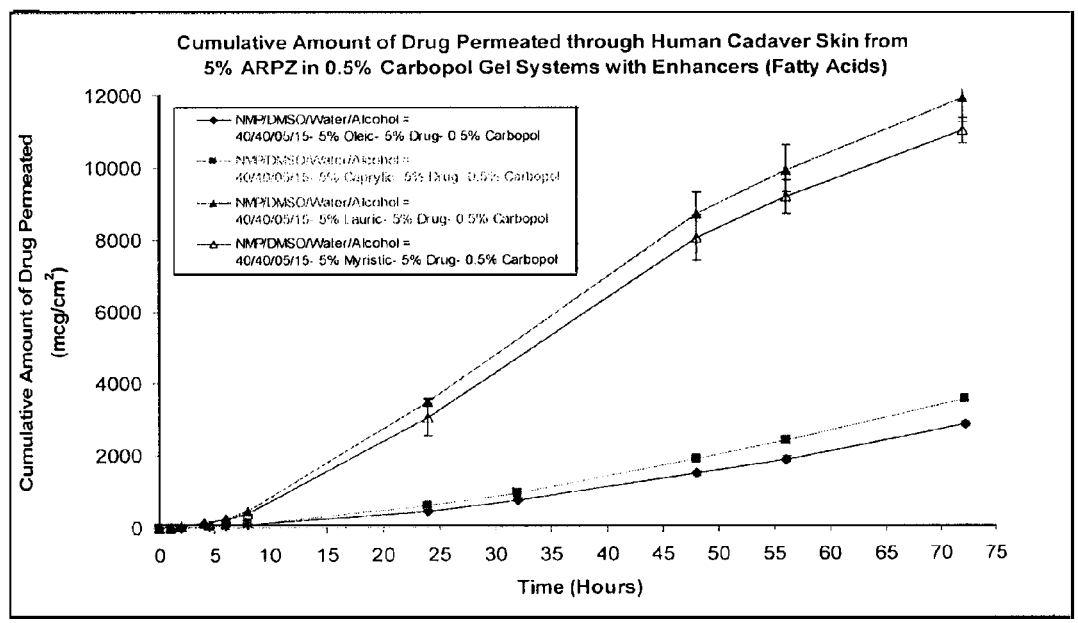
FIG. 3 is a chart showing the Cumulative Amount of Drug Permeated through Human Cadaver Skin from 5% ARPZ in 0.5% Carbopol Gel Systems with Enhancers (Fatty Acids).

The effect of enhancers on the flux of ARPZ through human cadaver skin was evaluated and is shown in FIG. 3. The desired optimum composition of ARPZ gel formulation contained Laurie and Myristc acid. Apart from Lauric and Myristc acid enhancer, the ARPZ transdermal delivery can be influenced by enhancers including but not limited to water, sulfoxides, and similar chemicals, dimethylsulfoxide (DMSO), dimethylacetamide (DMAC), dimethylformamide (DMF), decymethylsulfoxide (DCMS) etc, azone, pyrrolidones N-methyl-2-pyrrolidone (NMP), 2-pyrrolidon (2p), etc., fatty acids esters (butyl ethanoate, ethyl ethanoate, ethyl oleate, isopropyl myristate, isopropyl palmiate, methyl ethanoate etc), fatty acids (capric, caprylic, lauric, oleic, myristic, linoleic, stearic, palmitic etc), alcohols, fatty alcohols and glycols (nathanol, dodecanol, propylene glycols, glycerol etc), urea, essential oils, terpene and terpenoids (limonene, thymol, cineole etc), liposomes, niosomes, transferomes, ethanosomes etc.

Example

The effects of on the permeation of ARPZ through human cadaver skin were evaluated and a characteristic graph is shown in FIG. 2. The preferred optimum composition of ARPZ gel transdermal formulation had a pH in the range of approximately 6 to 7. Other than these optimal pH values, the ARPZ transdermal delivery may be influenced by pH values outside of the preferred range, but to a lesser extent. Thus, the present invention may still be achieved outside of the preferred pH range of approximately 6 to 7, depending upon the circumstances of use.

The systems of this discovery can deliver ARPZ at a flux between 50 mcg/ch-2. h and 800 mcg/ch-2. h, which can produce the required therapeutic ARPZ blood levels. Flux rate can be changed by modifying such parameters as ARPZ initial concentration, surface area of the patch, pH of the formulation, vehicle composition, enhancer type and composition, etc., in accordance with the teachings of the present invention.

Optimum therapeutic outcome requires not only a proper drug selection but also an effective drug delivery. Psychotropic drug compliance of rigorous regular medication schedules is of great importance. In many instances, oral administration of psychotropic agents is considered a less than optimal delivery system due to patient non-compliance[5]. Transdermal delivery of psychotropic drugs, especially with prolonged duration of action, would be valuable in increasing medication compliance, especially in the geriatric population. Further, potential advantages of ARPZ transdermal delivery are as follows: lack of hepatic first pass effect; eliminating the potential for over- or under-dosing; allowing the flexibility of terminating the drug administration by simply removing the patch; providing a simplified therapeutic regimen, thereby assisting medication compliance in the geriatric population.

REFERENCES

1. Inoue, T., Domae, M., Yamada, K., and Furukawa, T. Effects of the novel antipsychotic agent 7-([4-2,3-dichlorophenylo-1-piperazinyl]b Neuroutyloxyo-3,4-dihydro2 (1H)-quinolinone (OPC-14597) on prolactin release from the rat anterior pituitary. J. Pharmacol. Exp. Ther. 1996; 277(1):137-143.
2. Burris, K. D., Moiski, T. F., Ryan, E., Xu, C., Tottori, K., Kikuchi, T., Yocca, F. D, and Molinoff, P. B. Aripiprazole is a high affinity partial agonist at human D2 dopamine receptors. Int. J. Neuropsychopharmacol. 2000; 3(Suppl.1), S129.
3. Petrie, J. L., Saha, A. R., and McEvoy, J. P. Aripiprazole, a new atypical antipsychotic: Phase II clinical trial results. Eur. Neuropsychopharm 1997; 7 (Suppl 2): S227.
4. Saha, A. R., McQuade, R., Carson, W. H., Ali, M., W., Durbar, G. C., and Ingenito, G. Efficacy and safety of Aripiprazole and Risperidone vs. Placebo in patients with schizophrenia and schizoaffective disorder. World J. Biol Psych 2001; 2 (Suppl 1): 305S.
5. Geeta, A., Sanju, D., Psychotropic Drugs and Transdermal Delivery. An Overview. Int. J. of Pharma and Bio Science, 2001; V 1(2).

The invention claimed is:

1. A pharmaceutical composition comprising aripiprazole in a dosage form for transdermal delivery, wherein the composition comprises:

aripiprazole in the amount of 1 to 20% w/v;

an enhancer; and a gelling agent in the range of about 0.1% to 5% w/v, said gelling agent selected from the group consisting of natural polymers, semisynthetic polymers, synthetic polymers, carboxyvinyl polymers, carbomers, polyacrylic acid polymers, poloxamer, polyacrylamide, polyvinyl alcohol, polyethylene and co-polymers thereof, and combinations thereof;

wherein the dosage form is selected from the group consisting of a patch, an ointment, a cream, an emulsion, and a liposome, and further wherein the pH of the composition is approximately 6 to 7, further comprising approximately 40% N-methyl-2-pyrrolidone, approximately 40% Dimethylsulfoxide, approximately 15% alcohol, and approximately 5% water.

2. The pharmaceutical composition of claim 1 wherein the aripiprazole is in a gel or liquid form.

3. The pharmaceutical composition of claim 1 being in the form of a liquid and comprising an alcohol, glycol, mineral oil, and/or vegetable oil.

4. The pharmaceutical composition of claim 1 wherein the enhancer is selected from the group consisting of lauric acid, myristc acid, water, sulfoxides, dimethylsulfoxide, dimethylacetamide, dimethylformamide, azone, pyrrolidones, fatty acid esters, fatty acids, alcohols, fatty alcohols and glycols, urea, essential oils, terpene and terpenoids, liposomes, niosomes, transferomes and ethanosomes.

* * * * *